Figure 1:
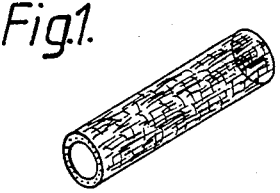

United States Patent [19]

Bornat

[11] Patent Number: 4,689,186
[45] Date of Patent: Aug. 25, 1987

[54] PRODUCTION OF ELECTROSTATICALLY SPUN PRODUCTS

[75] Inventor: Alan Bornat, Lancashire, England

[73] Assignees: Imperial Chemical Industries PLC, Millbank; Univ. of Liverpool, Liverpool, both of England

[21] Appl. No.: 804,333

[22] Filed: Dec. 5, 1985

Related U.S. Application Data

[63] Continuation of Ser. No. 695,421, Jan. 28, 1985, abandoned, which is a continuation of Ser. No. 525,429, Aug. 22, 1983, abandoned, which is a continuation of Ser. No. 298,257, Aug. 31, 1981, abandoned, which is a continuation of Ser. No. 82,759, Oct. 9, 1979, abandoned.

[30] Foreign Application Priority Data

Oct. 10, 1978 [GB] United Kingdom ............... 40029/78

[51] Int. Cl.⁴ ..................... B29B 13/08; B29C 35/08; B29C 41/08
[52] U.S. Cl. .......................................... 264/6; 264/10; 264/24; 264/115; 425/174.8 E
[58] Field of Search ............... 264/6, 24, 26, 8, 40.7, 264/121, 309, 310, 209.2, 10, 115, D75, 209.1, 209.5; 425/174.8 E

[56] References Cited

U.S. PATENT DOCUMENTS

| | | | |
|---|---|---|---|
| 2,116,942 | 5/1938 | Formhals | 18/8 |
| 2,467,213 | 4/1949 | Luaces | 260/41.5 |
| 3,280,229 | 10/1966 | Simons | 264/10 |
| 3,478,387 | 11/1969 | Ruekberg | 18/5 |
| 3,593,074 | 7/1971 | Isakoff | 317/262 A |
| 4,043,331 | 8/1977 | Martin et al. | 128/156 |
| 4,044,404 | 8/1977 | Martin et al. | 3/19 |
| 4,069,026 | 1/1978 | Simm et al. | 55/6 |
| 4,113,812 | 9/1978 | Talbott et al. | 264/24 |
| 4,143,196 | 3/1979 | Simm et al. | 428/212 |
| 4,223,101 | 9/1980 | Fine et al. | 528/76 |
| 4,230,650 | 10/1980 | Guignard | 264/24 |
| 4,287,139 | 9/1981 | Guignard | 264/10 |
| 4,323,525 | 4/1982 | Bornat | 264/24 |
| 4,345,414 | 8/1982 | Bornat et al. | 53/425 |
| 4,432,916 | 2/1984 | Logan | 264/24 |
| 4,474,630 | 10/1984 | Planck et al. | 156/62.4 |

FOREIGN PATENT DOCUMENTS 0357301 12/1972 U.S.S.R. ................... 264/24

Primary Examiner—Jan H. Silbaugh
Assistant Examiner—Karen D. Kutach
Attorney, Agent, or Firm—Cushman, Darby & Cushman

[57] ABSTRACT

Preparation of products having a tubular portion comprising electrostatically spinning a fiberizable liquid, the electrostatic field being distorted by the presence of an auxiliary electrode, preferably so as to encourage the deposition of circumferential fibers.

10 Claims, 7 Drawing Figures

PRODUCTION OF ELECTROSTATICALLY SPUN PRODUCTS

This is a continuation of Ser. No. 695,421 filed Jan. 28, 1985, now abandoned, as a continuation of Ser. No. 525,429 filed Aug. 22, 1983, now abandoned, as a continuation of Ser. No. 298,257 filed Aug. 31, 1981, now abandoned, as a continuation of Ser. No. 82,759 filed Oct. 9, 1979, now abandoned.

This invention relates to tubular products and to processes for the production thereof.

It is known to prepare specifically vascular prostheses, by a process involving the electrostatic spinning of liquids to give fibers which are then collected upon a shaped former, which may be a rod or tube of configuration corresponding to that which it is desired to impart to the internal surface of the product.

The process of electrostatic spinning involves the introduction of a liquid into an electric field whereby the liquid is caused to produce fibers which tend to be drawn to a charged receiver. While being drawn from the liquid the fibers usually harden, which may involve mere cooling (where the liquid is normally solid at room temperature, for example), chemical hardening or evaporation of solvent. The fibers obtained by electrostatic spinning are thin, and for the purpose of the invention they are usually of the order of 0.1 to 25 $\mu$m preferably 0.5 to 10 $\mu$m, more preferably 1.0 to 5 $\mu$m and particularly preferably 1 $\mu$m$\pm$20% in diameter. We have also found that for use in biological locations e.g. where they are likely to contact living tissue, the use of fibers of smaller diameter, i.e. less than 5 $\mu$m preferably less than 2 $\mu$m and particularly about 1 $\mu$m is advantageous.

The above mentioned patent application describes inter alia the production of tubular fibrous products or products comprising a tubular portion, using the technique of electrostatic spinning, and particularly the electrostatic spinning of fiber-forming compositions comprising a polyurethane, so that tubular products comprising polyurethane fibers having the above mentioned dimensions are obtained. Preferably substantially all of the electrostatically spun fibers of the product are of polyurethane material. One example of such a tubular product is a vascular prosthesis, particularly a synthetic blood vessel. Other applications for such tubular products include use as ducts of a variety of kinds, e.g. urinary and bile as well as tubular components of structures of other configuration, for example, heart components and components of auxiliary medical equipment, particularly where contact, especially lengthy contact, with living tissue is envisaged. Such tubular products are particularly valuable where intermittent stretching or swelling of the product, such as may result from pulsed flow of liquid therethrough, is likely to occur.

We have previously prepared tubular structures by using as the charged former or collector a tube or rod, conveniently rotating, during said preparation, about its longitudinal axis. We have found that in such a process the product obtained sometimes displays a pattern of fiber deposition which tends to be longitudinal (i.e. parallel to the long axis of the tube) rather than circumferential and its is conjectured that the force field generated by the charge on the collector is such that this disposition is obtained. This is shown in FIG. 1. In FIG. 1 and in FIG. 2 the trend of distribution is exaggerated for the purpose of illustration.

The present invention provides an improvement on the method and product of the aforementioned earlier application.

Figure 2:
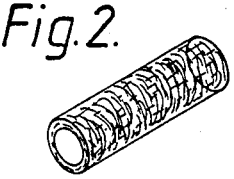

One object of the process of the present invention is to so modify the force field about the charged collector that the fibers are deposited thereon in a pattern different from that described above, preferably so that a higher proportion of the fibers have a generally circumferential rather than longitudinal disposition (see FIG. 2).

Accordingly one aspect of the present invention provides a process for the preparation of products comprising a tubular portion which process comprises the step of introducing into an electrostatic field a liquid comprising a fiberizable material, whereby the material is caused to produce fibers which tend to be drawn to a collector charged relative to the said fibers upon which they are deposited to form the said products, said electrostatic field being distorted by the presence of at least one auxiliary electrode.

It will be appreciated that the degree or magnitude and the form of modification of the field by the employment of the auxiliary electrode(s) according to the invention may be varied between very wide limits. As the mechanical properties of the product will reflect to some extent at least the disposition and proportion of fibers it contains it will be understood that the invention provides a method whereby tubular fibrous products may be prepared having a range of properties lying between the extremes in which a greater majority of the fibers tend to lie substantially in the circumferential or longitudinal direction. Since the strength or elastic modulus of the product is influenced by the disposition of the fibers constituting it, it is possible by control of the disposition of the fibers to control the strength and elasticity of the product in any particular direction. For example, where it is important that the product should have a particularly high longitudinal strength most of the fibers will preferably be predominantly longitudinal whereas where it is important that a tube should have a high bursting strength, a higher proportion of circumferential fibers may be appropriate. In this way, it is possible to prepare a product having known and predetermined strength and elastic characteristics, which may be important in matching to, say, a particular location in the vascular tree.

In general we prefer that not more than about 25% of the fibers in the product should lie predominantly in any one direction, i.e. that the product comprises fibers in both longitudinal and circumferential directions to provide both longitudinal and bursting strength.

The location and size of charge on the auxiliary electrode(s) may vary between wide limits and the precise level of charge and balance of charge on the different charged components will be determined quite easily by simple trial, the object of such location and charge being merely to effect desirable alteration in the electrostatic field such that the chosen fiber disposition is attained in the product. Indeed we have found it possible, by actual observation of the fiber pattern during spinning, to "tune" the apparatus by varying the absolute and relative levels of charge on the collector and auxiliary electrodes, as well as the relative positions of the charged components, to give a desired fiber distribution and disposition and to effect optimum deposition upon the collector.

Figure 3:
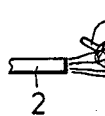

Thus, in one process, we have employed an arrangement of a plurality of linked auxiliary electrodes as shown diagrammatically in FIG. 3, where 1 is the charged collector, 2 is a means of introducing fiberizable material into the electrostatic field and 3 is a grid of auxiliary electrodes. We may employ one or more auxiliary electrodes, which may be electrically connected or separate, and that they may be of any convenient physical form, e.g. rods (parallel or otherwise to the collector), grids, networks of electrodes, etc. Obviously an auxiliary electrode arrangement will be chosen such that the flow of air to the fibers is not undesirably impeded.

The auxiliary electrode(s) may be of any appropriate material, usually a metal, and may be of any appropriate dimension. Thus, we have found it convenient to employ as the electrode one or more steel rods of diameter 1 to 10 mm 5 to 50 cm long, either singly or arranged to provide a grid with a spacing of 1 to 10 cm and alternatively an electrode comprising steel wire grids of cell size 5 cm. The auxiliary electrode(s) may be of any convenient shape; thus the grid may be substantially planar or it may be, for example, dished or curved.

The charge on the auxiliary electrodes may be of either sign, depending upon the precise effect upon the deposition pattern that may be required. Where two or more auxiliary electrodes are employed the charge and the size of charge on them may be the same or different, depending upon the effect upon the fiber deposition pattern that it is desired that the auxiliary electrodes should bring about. Such effects can be determined by simple trial.

We prefer to employ an auxiliary electrode having a charge of the same sign as that on the collector, but smaller, For example we have found it convenient to employ a collector charged to, say, 8 to 20 KV (relative to the source, and (−) or (+)) and an auxiliary electrode charged to about 4 or 5 KV less.

Figure 5:
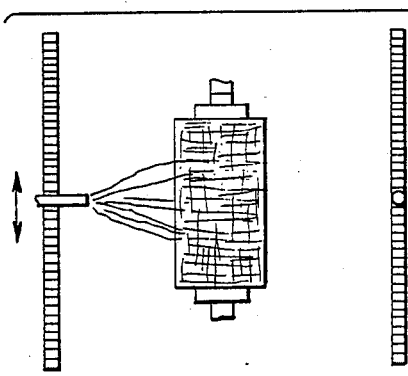

The auxiliary electrodes may be stationary in relation to the collector, but we do not exclude the possibility that they may move during production of the product. Such movement may occur throughout spinning or it may occur otherwise, during only part of the process and it may be continuous or discontinuous. We have found it advantageous, for example, where the fiberizable liquid is introduced into the field from a moving hollow needle for an auxiliary electrode to move in accord with the needle, for example in unison with it (see FIG. 5).

Figure 6:
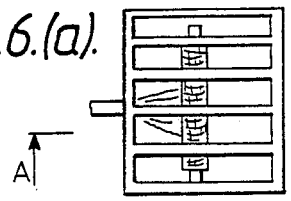
Figure 6B:
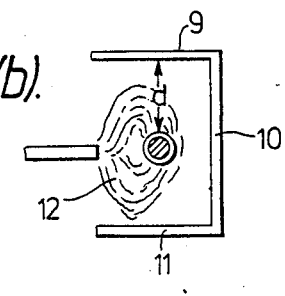

In a preferred electrode configuration the auxiliary electrode is shaped and disposed so that it generates a field which encourages separation of the electrostatically spun fibers one from another as they are formed, the shape on the collector, however, being dominant so that fibers are deposited thereon. This arrangement is advantageous also in that by encouraging separation of the fibers it makes possible the use of an array of spinnarets closer together than would otherwise be desirable because of possible interference and even adhesion of the fibers one to another. This also makes possible, of course, the use of a higher concentration of spinnarets. A particularly convenient auxiliary electrode configuration for this purpose is illustrated in FIG. 6, in which the auxiliary electrode effectively encloses the collector on three sides although in such an arrangement the rear most electrode component (10) may be omitted. Again, we have found it possible to control the deposition pattern by varying the charge and position distance of the electrode components one from another. In the electrode arrangement illustrated in FIG. 6, for example, the auxiliary electrodes may be effectively one, held at the same potential, or they may be charged to different potentials, depending upon the fiber pattern desired.

In particular, we have found that certain auxiliary electrode arrangements are advantageous in that they tend to cause the fibers to be stretched with the consequence that they are deposited upon the collector in an extended form. Upon removal from the collector if the fibers are sufficiently elastic they shorten and tend to cause the tubular component of the product to be reduced in diameter.

Thus according to yet a further embodiment of the invention the electrostatic field is so distorted by the presence of the auxiliary electrode that stretching of the spun fibers occurs and the stretched fibres so formed are deposited upon the collector so that upon removal of the collector from within the lumen of the product a reduction in the diameter of the lumen occurs as a consequence of shortening of the said stretched fibers.

In particular the invention provides a method of preparing tubular products of a diameter smaller than that of the collector upon which they are spun by introducing into the electrostatically spun product such a proportion of fibers particularly of an appropriate elasticity, that upon removal of the formed tube from the collector the diameter of the tube decreases, presumably as a consequence of the elasticity of the fibers. This is particularly important in the preparation of very fine bore tubes which otherwise are difficult to manufacture. Conveniently the tubular portion is reduced in diameter upon removal from the collector by at least 10%, preferably by at least 25% and more preferably at least 40% and possibly at least 50% or even more.

Thus, the invention provides a method of preparing products comprising a tubular component, particularly products comprising a tubular component of the order of a very few mm, say between 1 and 3 mm or even less than 1 mm in internal diameter, although it is equally useful for the preparation of larger diameter tubular products, e.g. having an internal diameter between 3 and 30 mm or even greater, particularly between 3 and 10 mm in diameter. The amount by which the diameter of the tubular portion decreases, if at all, will be influenced by the proportion of substantially circumferentially disposed fibers as well as their elasticity, but such effects may be determined by simple trial, and consequent selection of an appropriately dimensioned collector, fiber distribution and composition to provide a product of a chosen dimension.

The dimensions of the product, and the thickness of the wall will be influenced by the intended application and particular physical properties required. Usually the tubular component of the product will have a wall thickness between 0.1 and 5 mm, preferably between 0.25 and 3 mm and preferably between 0.5 and 2 mm. For example, a vein replacement prosthesis may require a wall thickness as low as 0.2 or even 0.1 mm, whereas a replacement artery will usually have a wall at least 0.5 mm thick at its thinnest point.

The precise location of and charge on the auxiliary electrodes can vary widely, and we have found it particularly convenient to locate the auxiliary electrodes so that fibers are deflected out until they almost contact the electrodes, as shown diagrammatically in FIG. 6, and are then attracted to the collector. In an extreme case (for example where the lateral electrodes approach the fiber source or where the charge upon the lateral electrodes is only slightly, e.g. 2 to 3 KV less than on the collector) we have found that liquid spinning material may actually be attracted in droplets to the auxiliary electrodes and fibers may then be pulled from these deposits to the collector. Such fibers also are often stretched and provide a method of producing a product having a bore which is reduced upon removal of the collector according to the invention. Obviously conditions will be avoided in which fiber are undesirably prevented from being collected upon the collector.

Although our preferred fiberizable material is polyurethane, other polymeric materials may be equally suitable, although their elastic properties may sometimes not be so advantageous. Thus, we have also used polyethylene terephthalate, fluorinated compounds, particularly fluorinated hydrocarbons, e.g. PTFE and silicones, polyamides, polyacrylonitrile, urea formaldehyde, etc. Where water-soluble polymers are employed a degree of cross-linking is advantageously induced to provide water insolubility. They may be spun from solutions or suspensions, as may be convenient. Polymers which in the fibrous state have a degree of elasticity are preferred for at least a proportion of the fibrous component of the product.

The technique of electrostatic spinning of liquids, including solutions containing a fiber forming material is known and has been described in a number of patent specifications, including U.S. Pat. No. 4,044,404 as well as in general literature, and information therein will be relevant to the operation of this invention.

While the foregoing description has referred to the preparation of products consisting of fibers, the invention is also applicable to the production of products comprising component(s) other than fibers obtained by electrostatic spinning. Such other components may themselves be fibrillar or non-fibrillar and may form an attachment to a tubular portion, which portion is prepared from electrostatically spun fibers, or the other component may itself be a component of the tubular portion of the product and may, for example, form an inner lining or an outer sheath or sleeve, or both, for the electrostatically spun fiber component.

Thus, the invention also provides a product comprising a first component which comprises electrostatically spun fibers and a second component which may be fibrillar or nonfibrillar and which is prepared by a technique other than electrostatic spinning. Such second component may, for example, be a woven fibrillar product, or it may form a sheet, e.g. a liquid impermeable layer of polymer. Any such material used in a prosthetic or other device to be used in contact with living body tissues will of course be biologically acceptable. Such other components may be formed before the spinning and collection of the electrostatically spun fibers, which may be spun onto the other component, where, for example, it is formed as a layer on the collector, or the other component may be applied to the electrostatically spun portion after its formation.

The product of the invention comprises an arrangement or pattern of fibers different from that of the product obtained in the absence of the auxiliary electrodes, and consequently will have properties different from such products.

The invention is further illustrated by the following examples.

EXAMPLE 1

Figure 4:
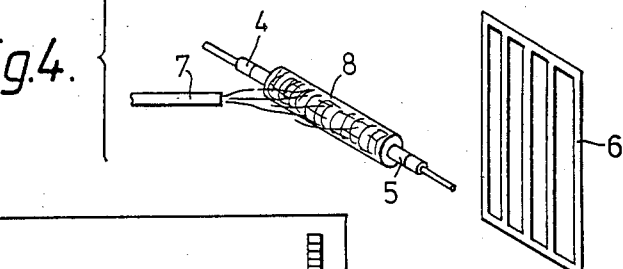

The apparatus was as shown diagrammatically in FIG. 4. The fiber collecting means consisted of a metal collector (charged to −12 KV) (mandrel) 4 mm in diameter (4) having a sheath of aluminium foil (5) 0.02 mm thick wrapped around it. The mandrel was rotated about its long axis at about 300 rpm.

An auxiliary electrode (6) consisting of a plurality of connected steel rods each 4 mm in diameter, 25 cm long, and 5 cm apart, was located 7 cm away from the collector and charged to −7 KV.

The fiber forming material was fed into the electric field surrounding the mandrel from a syringe (7) the needle of which was 3 cm long and 0.05 cm I.D. The fiber forming material was a polyester urethane block copolymer in DMF/Butanone solution. The dried solid polymer had a hardness within the range 30°–40° shore D.

Upon introduction of the polymer into the electric field the droplet instantly disintegrated into fibers which were drawn to the collector (over a distance of 10 cm against a counter current of air at 40° C. moving at about 100 ft/min) and deposited upon it in a tubular layer (8).

After allowing the layer to attain a thickness of about 2 mm the process was stopped, the collector removed from the apparatus, the aluminium and deposited fibrous tube slid off the collector and the sheath crushed and removed from the lumen of the fibrous tube.

Upon removal of the tubular product it was found that the diameter of the tube decreased to about 2 mm and the elastic modulus of the tube measured in a circumferential direction was greater than that of a similar tube prepared without using the auxiliary electrode.

EXAMPLE 2

The process of Example 1 was repeated except that the syringe was repeatedly traversed along the length of the collector as indicated in FIG. 6 (which is a plan view) and a single rod auxiliary electrode 4 mm in diameter and 20 cm long traversed similarly on the side of the collector away from the syringe.

EXAMPLE 3

The process of Example 1 was repeated except that the auxiliary electrode was shaped and disposed as shown in FIG. 6 (FIG. 6(a) is a plan view, FIG. 6 (b) is a sectional view along the line A—A in FIG. 6(a)). The auxiliary electrode was formed of three flat electrically connected grids (9, 10 and 11) of steel rods 4 mm in diameter and 2 cm apart. The distance "d" was 10 cm. The auxiliary electrode was charged to −8.5 KV and the collector to −12.5 KV. The path of the fibers is shown diagrammatically by dotted lines (12).

It will be appreciated that although the process has been described in the examples as using a single syringe or spinnaret a plurality of spinnarets may be employed to increase the rate of fibre formation.

The products of the invention find wide application, particularly in the medical field, as tubular devices for use in suitable locations, for example as prostheses of various kinds, e.g. vascular, and as synthetic urinary and bile ducts, as synthetic tracheae, and as tubes for a wide variety of other purposes.

According to a further aspect of the invention, therefore, there is provided a product for use in medical or veterinary applications, particularly as a prosthesis for incorporation into a living organism, for example as a component of the vascular tree, prepared by the process hereinbefore described. Products made by the process are found to take sutures well, without undue tearing, and not to leak unduly upon slight puncture.

What we claim is:

1. A process in which a liquid comprising a fiberizable material is introduced into an electrostatic field whereby the material produces fibers which are drawn to a collector which is charged relative to the fibers, and upon which they are deposited to form a product comprising a tubular portion having a proportion of the fibers lying circumferentially and in which the electrostatic field is distorted by the presence of an auxiliary electrode, characterised in that the auxiliary electrode is positioned and charged so that the proportion of fibers deposited in substantially circumferential disposition is increased relative to those so deposited in the absence of said auxiliary electrode and so that the fibers are stretched and deposited upon said collector in an extended form such that upon removal of the collector the tubular portion reduces in diameter.

2. A process according to claim 1 in which the collector is of cylindrical shape.

3. A process according to claim 1 in which the product is a tube.

4. A process according to claim 1 which at least one auxiliary electrode is located so that the collector is positioned substantially between said auxiliary electrode and the point at which the liquid is introduced into the electrostatic field.

5. A process according to claim 1 in which the auxiliary electrode carries a charge of the same sign as does the collector.

6. A process according to claim 1 in which the auxiliary electrode carries a charge smaller than that on the collector.

7. A process according to claim 6 in which the auxiliary electrode carries a charge between 2 and 8 KV less than that on the collector.

8. A process according to claim 1 in which the reduction in internal diameter is greater than 10%.

9. A process according to claim 1 in which the reduction in diameter is between 10 and 25%.

10. A process according to claim 1 in which the reduction in diameter is between 25 and 40%.

* * * * *